(12) United States Patent
Richard et al.

(10) Patent No.: US 10,433,767 B2
(45) Date of Patent: Oct. 8, 2019

(54) PEEL AND STICK CPR ASSISTANCE DEVICE

(71) Applicant: KONINKLIJKE PHILIPS N.V., Eindhoven (NL)

(72) Inventors: Christian James Richard, Shoreline, WA (US); Aaron James Piazza, Seattle, WA (US); Hans Patrick Griesser, Bainsbridge Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 490 days.

(21) Appl. No.: 14/363,202

(22) PCT Filed: Dec. 17, 2012

(86) PCT No.: PCT/IB2012/057381
§ 371 (c)(1),
(2) Date: Jun. 5, 2014

(87) PCT Pub. No.: WO2013/093757
PCT Pub. Date: Jun. 27, 2013

(65) Prior Publication Data
US 2015/0045697 A1 Feb. 12, 2015

Related U.S. Application Data

(60) Provisional application No. 61/578,351, filed on Dec. 21, 2011.

(51) Int. Cl.
*A61B 5/11* (2006.01)
*A61B 5/00* (2006.01)
*A61H 31/00* (2006.01)

(52) U.S. Cl.
CPC .............. *A61B 5/11* (2013.01); *A61B 5/6823* (2013.01); *A61B 5/742* (2013.01); *A61B 5/7455* (2013.01);

(Continued)

(58) Field of Classification Search
CPC ......... A61B 5/11; A61B 5/6823; A61B 5/742; A61B 5/6832–6833; A61B 5/7425;
(Continued)

(56) References Cited

U.S. PATENT DOCUMENTS

| 6,427,685 B1 * | 8/2002 | Ray, II ................. G09B 23/288 |
| | | 128/200.24 |
| 8,532,765 B2 | 9/2013 | Ochs et al. |

(Continued)

FOREIGN PATENT DOCUMENTS

| CN | 201370742 Y | 12/2009 |
| WO | 2008015623 A2 | 2/2008 |

OTHER PUBLICATIONS

"Guidelines 2000 for Cardiopulmonary Resuscitation and Emergency Cardiovascular Care", Currents in Emergency Cardiovascular Care, American Heart Association, vol. 11, No. 3, (2000), pp. 1-28.

*Primary Examiner* — Rene T Towa
*Assistant Examiner* — Benjamin S Melhus

(57) ABSTRACT

A cardiopulmonary resuscitation (CPR) assistance device (400) is described for use by a rescuer providing manual CPR. The device has a visual indicator (430, 418, 420, 422) arranged about its periphery, such that visual assistance to the rescuer can be provided regardless of the rescuer's hand position. The CPR assistance device also includes a staged method of providing visual assistance, such that increasingly urgent information is provided if the sensed CPR accuracy fails to improve.

20 Claims, 7 Drawing Sheets

(52) U.S. Cl.
CPC ......... *A61H 31/005* (2013.01); *A61H 31/007* (2013.01); *A61H 2031/002* (2013.01); *A61H 2201/5061* (2013.01); *A61H 2201/5084* (2013.01); *A61H 2201/5097* (2013.01)

(58) Field of Classification Search
CPC .. A61B 5/7445; A61B 5/7455; A61H 31/005; A61H 31/007; G09B 23/288; G06F 3/0488
See application file for complete search history.

(56) References Cited

U.S. PATENT DOCUMENTS

| | | | | |
|---|---|---|---|---|
| 9,092,995 | B2* | 7/2015 | Pastrick | G09B 23/28 |
| 2006/0270952 | A1* | 11/2006 | Freeman | A61H 31/007 |
| | | | | 601/41 |
| 2007/0152977 | A1* | 7/2007 | Ng | G06F 3/03547 |
| | | | | 345/173 |
| 2007/0270074 | A1* | 11/2007 | Aochi | A63H 11/00 |
| | | | | 446/175 |
| 2008/0146973 | A1 | 6/2008 | Lund et al. | |
| 2008/0312565 | A1* | 12/2008 | Celik-Butler | A61H 31/005 |
| | | | | 601/43 |
| 2009/0105605 | A1* | 4/2009 | Abreu | A61B 5/0008 |
| | | | | 600/549 |
| 2009/0176632 | A1* | 7/2009 | Wiber | A43B 1/0036 |
| | | | | 482/84 |
| 2010/0213042 | A1* | 8/2010 | Smidt | A47C 31/008 |
| | | | | 200/5 A |
| 2010/0256539 | A1* | 10/2010 | Strand | A61M 16/0084 |
| | | | | 601/41 |
| 2011/0130798 | A1* | 6/2011 | Elghazzawi | A61N 1/3925 |
| | | | | 607/5 |
| 2011/0201979 | A1* | 8/2011 | Voss | A61H 31/005 |
| | | | | 601/41 |
| 2012/0302844 | A1* | 11/2012 | Schnidrig | A61B 5/6833 |
| | | | | 600/309 |
| 2013/0220856 | A1* | 8/2013 | Roach | A45C 11/00 |
| | | | | 206/363 |

* cited by examiner

PEEL AND STICK CPR ASSISTANCE DEVICE

CROSS-REFERENCE TO PRIOR APPLICATIONS

This application is the U.S. National Phase application under 35 U.S.C. § 371 of International Application No. PCT/IB2012/057381, filed on Dec. 17, 2012, which claims the benefit of U.S. Provisional Patent Application No. 61/578,351, filed on Dec. 21, 2011. These applications are hereby incorporated by reference herein.

The invention relates generally to medical devices, and more particularly, to cardio-pulmonary resuscitation (CPR) assistance and training devices.

Cardiac arrest is a life-threatening medical condition in which the patient's heart fails to provide blood flow to support life. CPR can be administered to a patient experiencing cardiac arrest to cause blood to flow in the patient. A rescuer administers CPR by compressing the patient's chest interspersed with blowing into the patient's mouth to fill the lungs with oxygen. CPR can be combined with other forms of therapy as well, such as defibrillation therapy. Between the times defibrillation shocks are delivered to a patient, CPR is administered to promote blood flow.

Studies have suggested that a patient's survival prospects can be improved by the administration of high-quality CPR. The quality of the CPR is directly related to the quality of the chest compressions, a part of which is determined by compression depth, rate, and whether each compression is completely released during the upstroke. Good chest compressions are generally those which depress the chest of an adult by four centimeters and about two and a half centimeters for a child at a rate of about 100 compressions per minute. There are many guidelines known in the art that set out desired compression depths for CPR. See, for instance, Guidelines 2000 for Cardiopulmonary Resuscitation and Emergency Cardiovascular Care, 102 Circulation Supp. I (2000).

Learning to administer chest compressions of sufficient depth is traditionally part of CPR training. For example, in practice situations involving manikins, compression depth is commonly measured and the information fed back to the participant. It is assumed that by practicing chest compressions on a manikin, the participant will be capable of repeating the same movement pattern on real human patients. However, studies have shown that the ability to repeat the movement pattern of administering chest compressions is poor even immediately after being trained, and not surprisingly, becomes worse over time. Additionally, since human anatomy varies from person to person, patients have differing degrees of resistance to chest compressions and require different levels of force to sufficiently compress the chest. As a result, learning to administer chest compressions of uniform, correct compression depth through CPR training on a manikin is difficult to achieve. Thus, devices have been developed which assist a rescuer by providing information about the proper depth, rate and release of chest compressions during the administration of CPR. Such a device is shown for example in co-assigned U.S. patent application Ser. No. 12/514,474 entitled "CPR Coaching Device with Reduced Sensitivity to Motion." Similar devices appear in U.S. patent application Ser. No. 11/764,174 entitled "Cardiopulmonary Resuscitation Sensor" and U.S. patent application Ser. No. 11/640,436 entitled "System for Providing Feedback on Chest Compression in CPR." Each of the described devices illustrates a chest-applied CPR feedback sensor with a display on its face to guide the user in proper technique.

FIG. 1 illustrates a CPR coaching device 100 as shown in co-assigned U.S. patent application Ser. No. 12/514,474. The CPR coaching device 100 is operable to coach a rescuer in administering CPR to a patient by detecting CPR compression data and then providing feedback on whether the chest compression depth and rate are adequate.

An upper portion 120 of a housing 118 of the CPR coaching device 100 is shown in FIG. 1. An illustration 110 depicting a patient's torso is included on the upper portion 120 of the CPR coaching device 100 to illustrate the proper position and orientation of the CPR coaching device 100 on the patient during CPR. In this position the lower portion of the device 100 opposite the upper portion 120 is in contact with the torso of the patient. The CPR coaching device may be attached to the patient by an adhesive layer present on a lower portion of the housing 118 of the CPR coaching device 100. A cable 130 is used to couple the physiological and coaching information produced by the coaching device to another medical device, such as a coaching instruction enunciator or a defibrillator, to which the CPR coaching device 100 is attached.

The CPR coaching device provides feedback to the user either by means of a display placed on the face of the upper portion or via an external device connected to the CPR coaching device by cable 130.

As shown in FIG. 2, with the CPR coaching device 100 positioned on the sternum of a patient 210, a rescuer 220 applies chest compressions in a conventional manner using two hands with one placed over the other. Instead of placing the hands directly on the patient 210, however, the rescuer's hands are placed on the CPR coaching device 100 and chest compressions are applied to the patient 210 via the CPR coaching device 100. Chest compressions are administered by the rescuer 220 as prescribed by conventional CPR protocols. The CPR coaching device 100 measures the depth of each compression with an accelerometer and the force of each compression with a force sensor and provides visual feedback through the display on the device face.

As can be seen by inspection of FIG. 2, however, a problem arises. During use, the displayed feedback on the face of the CPR coaching device is easily obscured by the rescuer's hands. In addition, the displayed feedback may be difficult to read if the rescuer's position is out of orientation with the display orientation.

The problem is not resolved by providing the display remotely, either. During chest compressions, the rescuer's attention is properly directed to his hands and technique. By requiring the rescuer to watch an AED or other display located away from the focus of CPR, the rescuer may become distracted, or his technique may be negatively impacted by an awkward angle of observation. Therefore what is needed is a display for a CPR assistance device which provides visual information at the point of application which cannot be obscured by the rescuer's hands, nor is affected by the rescuer's position relative to the display.

The present invention is directed to a CPR assistance device which provides a visual display of the effectiveness of the applied CPR that is not affected by the presence of the rescuer's hands or by his position relative to the device. The device is preferably configured as a self-adhesive flexible patch which is to be applied to the patient's chest prior to beginning CPR.

It is thus one object of the present invention to provide a CPR assistance device with a visual display output that is arrayed around the periphery of the device.

Another object of the invention is to provide a CPR assistance device which is easier to use. The device supplements its inventive visual display with useful graphic instructions, automatic activation, and a dual-use release liner which also acts as a CPR ventilations bather.

It is yet another object of the invention to realize the benefits previously described in a low-cost, preferably disposable, CPR assistance device. Such a device can then be quickly deployed to the chest of a cardiac arrest victim, remain in place through hand-offs to subsequent advanced rescue teams, and be discarded after the rescue is complete, without needless expense. The inventive device can be realized with low cost LEDs, sensing elements, and controlling circuitry which can be mounted on a flexible substrate to fulfill this object.

Figure 1:
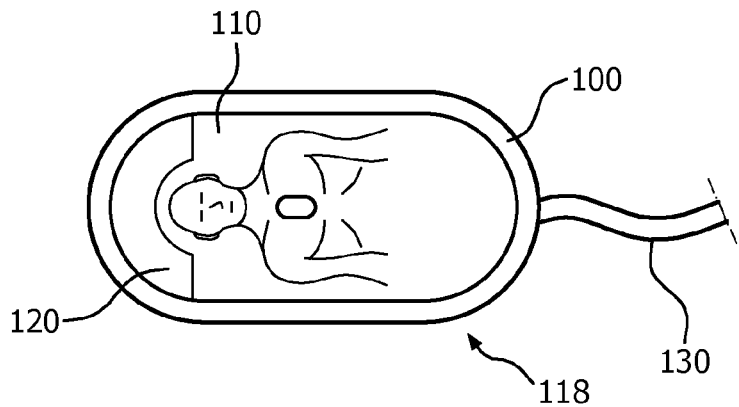
FIG. 1 is a diagram of a CPR coaching device.
Figure 2:
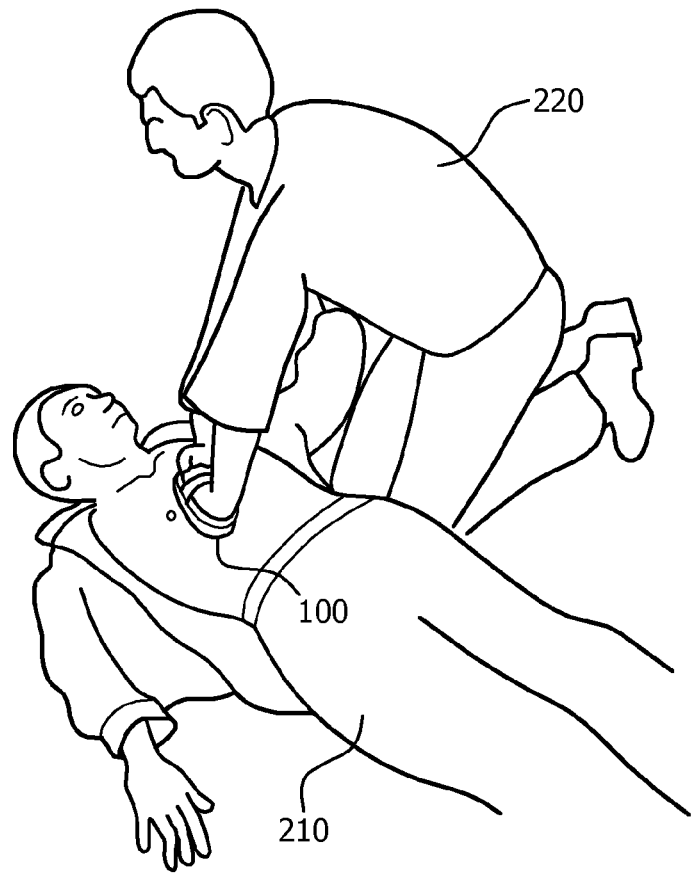
FIG. 2 illustrates a rescuer using a CPR coaching device.
Figure 3:
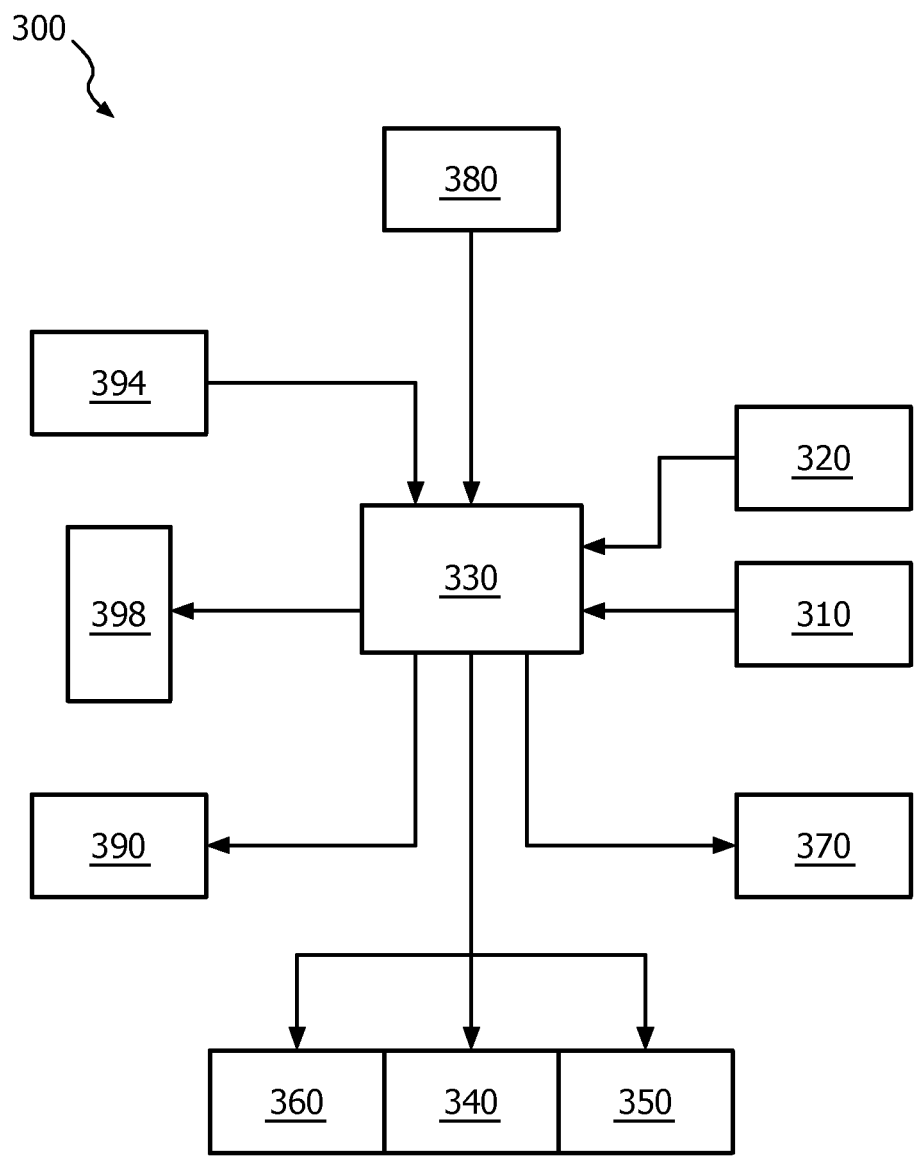
FIG. 3 illustrates a block diagram of components included in a CPR assistance device according to the principles of the present invention.

FIG. 3 is a block diagram showing a basic circuit arrangement of a CPR assistance device 300. An accelerometer 310 senses accelerations induced by the movement of the chest under compressions. A force sensor 320 senses the force applied to the CPR assistance device by the rescuer's hands. The force sensor 320 is preferably of a piezoelectric sensor film.

The accelerometer 310 and force sensor 320 provide acceleration and force signals to controller 330, which uses the signals to obtain CPR chest compressions data such as depth, rate, and complete release. Methods and algorithms used to convert the signals to the CPR data are well known in the art and will not be further described here. The protocols used by the controller 330 may be stored in flash memory on the device.

Controller 330 uses the calculated data to sense a condition of the ongoing CPR compressions and to provide and appropriate output indication to the user. For example, controller 330 may activate a first light 340 to blink at a rate corresponding to a desired rate of CPR compressions. If the desired rate and the calculated rate of CPR compressions differ meaningfully, controller 330 may instead activate a second light 350 in a second color to blink at the desired rate. If enough compressions have occurred, controller 330 could activate a third light 360 to blink at a third color signifying the desired number and rate of ventilations breaths. Controller 330 also can selectively control a vibratory element 370 which provides a tactile feedback to the rescuer. Each of the lights and the vibratory elements are preferably mounted on the device 300.

The CPR assistance device 300 incorporates an automatic activation feature in order to simplify its deployment. As will be described in more detail below, a deployment sensor 380 senses the separation of a release liner from the back of the device, and provides a corresponding input to controller 330. Controller 330, in a low-power standby mode until then, "wakes up" and activates its main functions. A power source 394 provides power to all of the components. The power source 394 is preferably a low-profile and lightweight battery, such as a coin cell battery or a thin film battery.

CPR assistance device 300 may optionally include a wireless transmitter 390 for providing user guidance to nearby wireless receivers via known methods such as Bluetooth™, Wi-Fi or infrared IRDA. Thus, information as displayed on the device itself could also appear simultaneously on handheld personal digital assistants, cardiac monitor/defibrillators, or portable computers, and be logged there for later analysis.

In addition to the lights 340, 350, 360 and the vibratory element 370, CPR assistance device 300 may optionally include an information display 398 on its front face. The information display 398 is preferably a simplified version of a known device display, substituting LED lights for LCD panel graphics.

Figure 4:
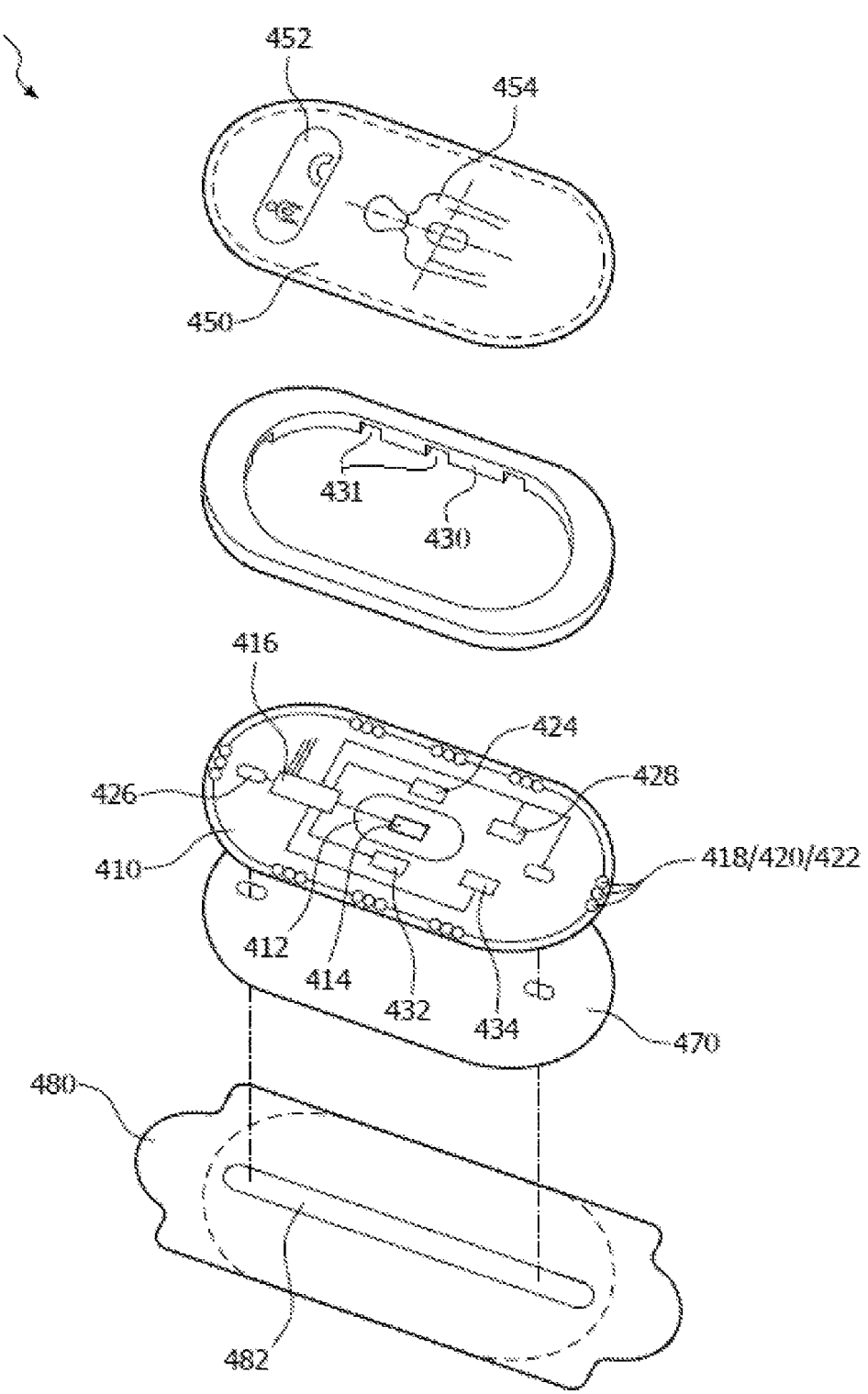
FIG. 4 illustrates an exploded view of a CPR assistance device according to the principles of the present invention.

FIG. 4 illustrates an exploded view of a CPR assistance device 400 of the present invention. CPR assistance device 400 is comprised of five subassembly layers generally stacked upon each other. The main control circuitry and components are disposed on a substrate 410. Substrate 410 is preferably of a flex-circuit material having mounted components connected by printed circuit traces. Force sensor 412 and accelerometer 414 are preferably mounted near the center of the substrate 410, around which controller 416, wireless transmitter 428, deployment sensor 426, vibratory element 424, and display controller 434 may be arranged.

FIG. 4 also illustrates an array of first lights 418, second lights 420 and third lights 422 arranged around the periphery of substrate 410. The lights are arranged to provide illumination generally co-planar with the substrate. In a most preferred arrangement, eight sets of lights, each set consisting of a different colored first, second and third light, are spaced equally around the periphery of substrate 410. Preferred colors for the lights are green for the first light 418, red for the second light 420, and blue for the third light 422.

Figure 6A:
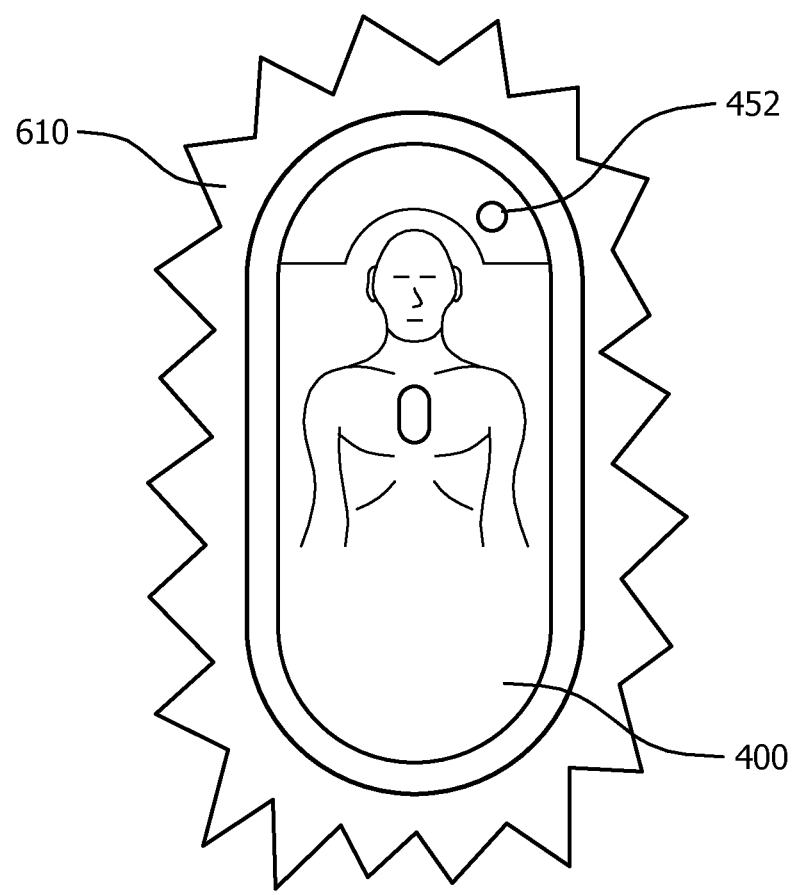
FIGS. 6a and 6b are top views of a CPR assistance device according to the principles of the present invention, showing the pattern and arrangement of the illumination enabled by the device.

Arranged above substrate 410 is visual output layer 430. Visual output layer 430 is comprised of a translucent or transparent flexible polymeric material which serves as a lens or light pipe for the first, second and third lights on substrate 410. Preferably, visual output layer 430 is disposed to diffuse and fan the illumination from lights 418, 420, 422 out of the edge surface and the top surface of the material. FIG. 6a illustrates. Further, its thickness dimension is slightly greater than the elevation of the lights 418,420,422 over the substrate 410. Visual output layer 430 may also be shaped with niches 431 to substantially cover each set of lights 418, 420, 422 to allow for a smaller footprint size of the device. Finally, visual output layer 430 may be of a ring-like shape such that the force sensor 412 on the substrate 410 may be engaged with the underside of the device top cover 450.

Top cover 450 is arranged over visual output layer 430 and substrate 410. It provides an engagement surface for the rescuer's hands, a placement graphic 454 printed thereon, and optionally includes a display 452. The objective of low-cost in the device gravitates toward the display comprising a printed facsimile of a more expensive CPR assistance device, but with display lights being one or more indicator LEDs. The underside of top cover 450 engages the force sensor 412.

Top cover 450 is preferably comprised of a thin and durable, printable, polymeric sheet. The center portion of the sheet should be opaque, but the peripheral edge of the sheet may be transparent or translucent to allow transmission of light from lights 418, 420, 422. As such, top cover 450 may be a laminated structure having the top sheet laminated concentric to a slightly larger clear sheet. Alternatively, the top sheet may be beveled to expose the underlying clear material.

An adhesive layer 470 is disposed under substrate 410. The adhesive is selected from a biocompatible material which can hold the device 400 securely to a patient's chest without causing skin damage or injury. FIG. 4 illustrates voids in the adhesive layer 470 which align with the deployment sensor 426 on the substrate 410. A conductive pathway through substrate 410 and the adhesive layer 470 electrically connect deployment sensor 426 to a conductive strip 482 disposed on the release liner 480 below.

Release liner 480 protects the adhesive in adhesive layer 470 until the device 400 is deployed for use. Release liner 480 is preferably constructed of a thin sheet of polymer or paper which is coated with a silicon release agent on the adhesive side. If the adhesive is susceptible to drying out, the release liner 480 can seal the material from the outside environment. The sheet is shaped to include tabs for easy grasping, such that the release liner 480 can easily be removed.

Release liner 480 preferably includes a conductive strip 482 disposed on the adhesive-facing side of the sheet. Deployment sensor 426 is electrically engaged with strip 482 when the release liner is in place. When release liner 480 is peeled away, deployment sensor 426 senses the broken circuit, and controller 416 automatically activates the device.

Figure 5A:
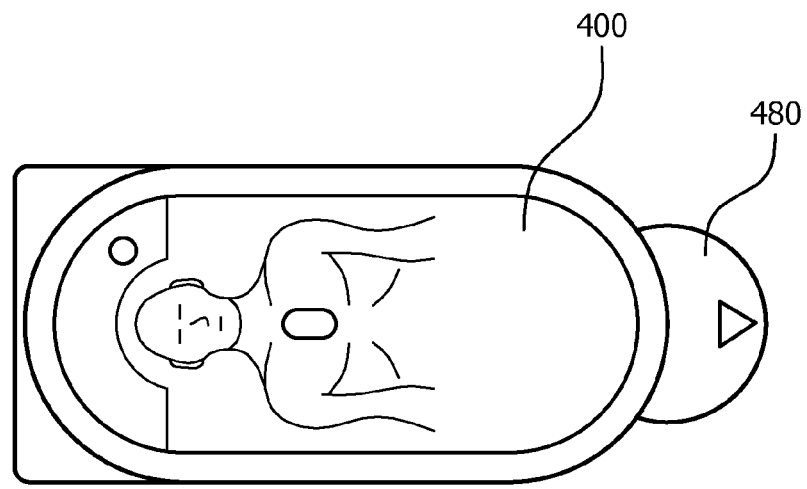
FIG. 5a is a top view.
Figure 5B:
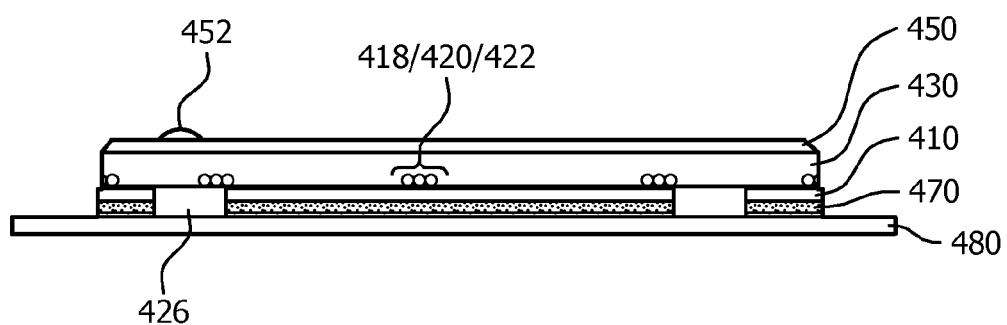
FIG. 5b is a side view of the assembled CPR assistance device according to the principles of the present invention.

FIG. 5a is a plan view and FIG. 5b is an edge view of the CPR assistance device 400 in its assembled and pre-deployed state. FIG. 5b shows each of the five layers: top cover 450, visual output layer 430, substrate 410, adhesive layer 470 and release layer 480. The electrical engagement of the deployment sensor 426 from substrate to release layer conductive strip is shown. Lights 418, 420, 422 and the slight protuberance of the optional LED in display 452 are shown.

As can be seen by FIG. 5b, the assembled device has a thin form factor which can be made quite flexible by means of the selected materials of construction. The arrangement permits compact storage and easy transport. In addition, a flexible device exerts less localized pressure on the patient, and provides better tactile connection between the rescuer's hand and the patient's chest. What is realized overall is better comfort for both participants in a device which more closely approximates traditional sensor-free CPR.

Figure 6B:
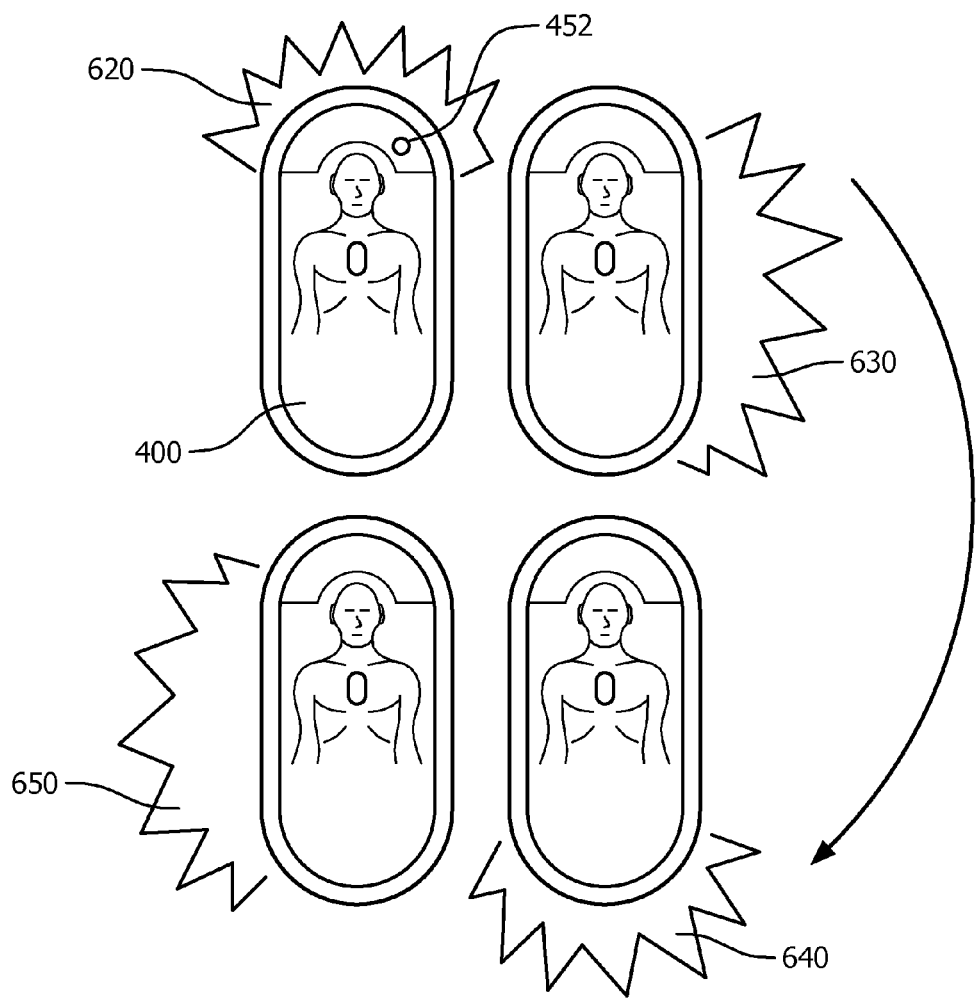

Now with reference to FIG. 6a and FIG. 6b, operation of CPR assistance device 400 is described. The CPR assistance device 400 is controlled by a concept of "rhythm feedback", which is defined as a type of CPR feedback which is patterned to be appropriate to a given task and contextual situation depending on a sensed condition of CPR. For example, the device 400 may indicate activation by vibrating with vibratory element 370, and then progress to a metronome-like green flashing first light 340 for a period of time appropriate for applying the device to a patient. If a second sensed condition of rate differs from a desired rate of compressions, are detected, controller 330 may begin a metronome-like red flashing from second light 350 at a desired rate of compressions. If no compressions are detected at all after an appropriate time, the device may begin issuing an alternating red and green flashing from first and second lights 340, 350. If subsequent proper compressions are detected, the device 400 may revert to the green flashing at first light 340.

Some CPR protocols call for rescue breathing, i.e. ventilations, after a period of chest compressions. Device 400 assists in such a protocol by activating third light 360 after the controller determines that an appropriate number or duration of compressions has been applied. Third light 360, preferably in blue, flashes at the desired ventilation rate and number. The CPR compressions cycle then resumes.

Many variations of the above-described visual feedback fall within the scope of the invention. For example, different patterns of flashing lights may be appropriate depending on the sensed condition of CPR. Repeating pauses may be inserted into the flashing cycle to realize a "Flash-flash-pause" or "flash-flash-flash-pause" appearance, for example. Use of vibration in concert with one or more light patterns is also contemplated for certain sensed conditions of CPR, such as a "good CPR" determination.

FIG. 6a illustrates the flashing output 610 from CPR assistance device 400 at its periphery. An LED at display 452 may optionally operate in concert with the flashing output 610. By this arrangement, regardless of where the rescuer's hands are placed over the face of device 400 to perform compressions, the peripheral flashing always remains visible. The rescuer can thus respond and correct his CPR technique at any time during the rescue.

FIG. 6b illustrates an alternate mode of operation in the CPR assistance device 400. In this embodiment, lights grouped and arrayed around the periphery of device 400 are sequentially flashed to create a rotating light effect. Top side illumination 620 occurs first, right side illumination 630 second, bottom side illumination 640 next, followed by left side illumination 650, and so on. The rotating light effect can be matched to a desired rate, for example to the desired rate of compressions. If the sensed and desired rates differ substantially, the color of the rotating light effect can be changed by activating the second light in each group. In addition, patterns of different colored lights can be interleaved into the rotation to represent a particular sensed condition. Display 452 may be operated in concert with the rotating pattern. Variations of the rotating pattern fall within the scope of the invention.

Figure 7:
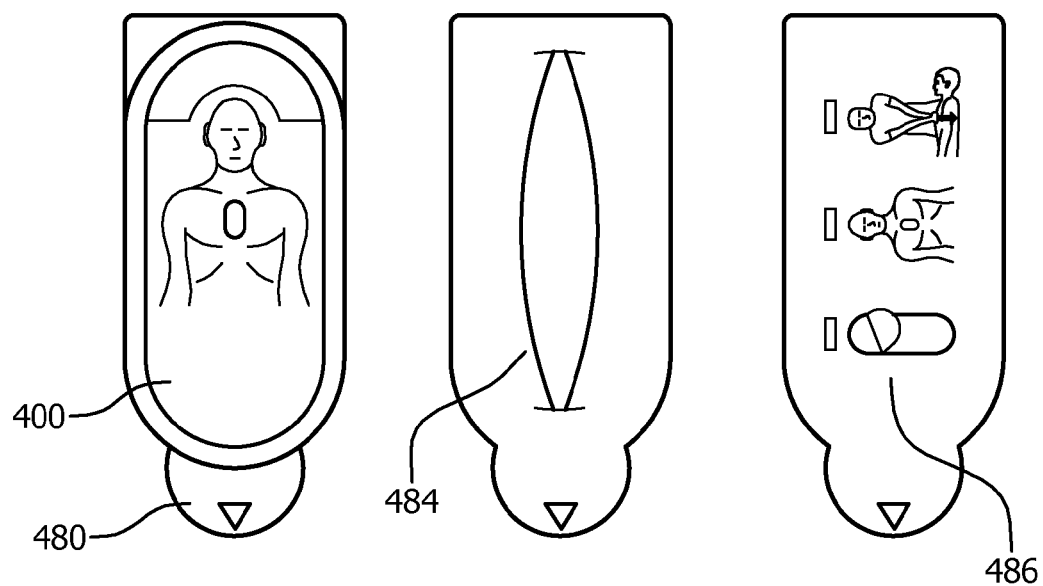
FIG. 7 illustrates two embodiments of a release liner portion of the CPR assistance device according to the principles of the present invention.

FIG. 7 illustrates additional useful embodiments of the device 400 release liner 480. One variation, release liner 484, includes an elongated slit or void. The slit allows the release liner 484 to be placed over the patient's mouth during a rescue to serve as a ventilation breaths bather. Appropriate use instructions may also be printed on the release liner 484. Another embodiment, release liner 486, includes graphic instructions printed on the liner for use in assisting the rescuer in the steps of the CPR.

Variations to the aforedescribed apparatus and method are considered to fall within the scope of the claimed invention. For example, the particular number and arrangement of the components on the substrate, or the particular size, shape, and appearance of the device may differ within the scope of the invention.

What is claimed is:
1. A cardiopulmonary resuscitation (CPR) assistance device comprising:
   a substrate;

an accelerometer mounted on the substrate and operable to detect motion related to a CPR chest compression;
a force sensor mounted on the substrate and operable to detect a force related to the CPR chest compression;
a controller mounted on the substrate and disposed in electrical communication with the accelerometer and force sensor;
a translucent or transparent visual output layer disposed over the substrate and having an edge surface normal to the substrate and around a periphery of the substrate, the visual output layer having a light with a first color, wherein an activation of the light is controlled by the controller, and wherein the visual output layer comprises a niche disposed to cover the light, the visual output layer also having a thickness sufficient to diffuse and fan illumination from the light out of the edge surface and co-planar with the substrate; and
a top cover disposed over the visual output layer and disposed to provide an engagement surface between a rescuer's hands and the force sensor,
wherein the light is operable to illuminate the peripheral edge surface of the visual output layer to assist in the application of CPR.

2. The cardiopulmonary resuscitation (CPR) assistance device of claim 1, wherein the light comprises a plurality of LEDs arranged around the periphery of the visual output layer.

3. The cardiopulmonary resuscitation (CPR) assistance device of claim 2, wherein the controller is operable to flash the light at a desired rate of CPR compressions.

4. The cardiopulmonary resuscitation (CPR) assistance device of claim 3, further comprising a second plurality of LEDs having a second color and arranged around the periphery of the visual output layer, wherein the controller is operable to flash the second plurality of LEDs at the desired rate of CPR compressions if the desired rate differs from a sensed rate of CPR compressions by a predetermined amount.

5. The cardiopulmonary resuscitation (CPR) assistance device of claim 2, wherein the controller is operable to sequentially flash each individual LED of the plurality of LEDs in a pattern having a cycle corresponding to a desired rate of CPR compressions.

6. The cardiopulmonary resuscitation (CPR) assistance device of claim 5, further comprising a second plurality of LEDs having a second color and arranged around the periphery of the visual output layer, wherein the controller is operable to sequentially flash each individual LED of the second plurality of LEDs in a pattern having a cycle corresponding to the desired rate of CPR compressions if the desired rate differs from a sensed rate of CPR compressions by a predetermined amount.

7. The cardiopulmonary resuscitation (CPR) assistance device of claim 4, further comprising a third plurality of LEDs having a third color and arranged around the periphery of the visual output layer, wherein the controller is operable to flash the third plurality of LEDs at a desired rate of ventilations.

8. The cardiopulmonary resuscitation (CPR) assistance device of claim 1, further comprising a second light having a second color,
wherein the controller senses a condition of the CPR compression and selectively controls the light and the second light according to the sensed condition.

9. The cardiopulmonary resuscitation (CPR) assistance device of claim 8, further comprising a vibratory element operable to provide tactile feedback to the top cover, wherein the controller selectively controls the vibratory element according to the sensed condition.

10. The cardiopulmonary resuscitation (CPR) assistance device of claim 1, further comprising:
an adhesive backing layer disposed on the side of the substrate opposite the visual output layer, the adhesive operable to adhere the device to a patient's chest; and
a removable release liner disposed over the adhesive backing layer to protect the adhesive prior to use.

11. The cardiopulmonary resuscitation (CPR) assistance device of claim 10, further comprising a deployment sensor in electrical communication with the controller, and wherein the removable release liner further comprises a conductive strip disposed to be in electrical communication with the deployment sensor, and further wherein the controller activates the device when the deployment sensor and the conductive strip are separated.

12. The cardiopulmonary resuscitation (CPR) assistance device of claim 11, wherein the release liner comprises a ventilations barrier.

13. The cardiopulmonary resuscitation (CPR) assistance device of claim 12, further comprising CPR assistance graphic instructions disposed on the release liner.

14. The cardiopulmonary resuscitation (CPR) assistance device of claim 1, further comprising a wireless transmitter disposed on the substrate in controllable communication with the controller, the transmitter further comprising either a Bluetooth transmitter or a Wi-Fi transmitter.

15. A method for providing assistance in the administration of cardiopulmonary resuscitation (CPR) to a patient comprising the steps of:
providing the CPR assistance device of claim 2;
applying the CPR assistance device to the patient;
and illuminating the plurality of LEDs in a pattern depending on a sensed condition of CPR.

16. The method of claim 15, wherein the CPR assistance device has a second plurality of LEDs in a second color and further comprising a step of illuminating the second plurality of LEDs in a pattern depending on a second sensed condition of CPR.

17. The method of claim 16, wherein the CPR assistance device has a vibratory element, and further comprising a step of actuating the vibratory element depending on a third sensed condition of CPR.

18. The method of claim 15, further comprising the steps of:
removing a release layer from a backing layer on the CPR assistance device prior to the applying step; and
deploying the release layer to the patient mouth for use as a CPR ventilations barrier.

19. The method of claim 16, wherein the CPR assistance device has a third plurality of LEDs in third color and further comprising a step of illuminating the third plurality of LEDs at a desired rate of ventilations.

20. The method of claim 15, further comprising the steps of:
removing a release layer from a backing layer on the CPR assistance device prior to the applying step;
sensing the removal of the release layer from the backing layer; and
activating the CPR assistance device based upon the sensing step.

* * * * *